United States Patent [19]
Hettick

[11] 4,084,586
[45] Apr. 18, 1978

[54] TUBULAR SUPPORT FOR ENCLOSING A BODY MEMBER

[76] Inventor: Lon R. Hettick, 5050 Garford, Long Beach, Calif. 90815

[21] Appl. No.: 731,616

[22] Filed: Oct. 13, 1976

[51] Int. Cl.² .............................................. A61F 13/00
[52] U.S. Cl. .................................. 128/157; 128/80 C; 128/80 H; 128/165
[58] Field of Search ............. 128/157, 165, 166, 80 C, 128/80 H, 293, 155

[56] References Cited

U.S. PATENT DOCUMENTS

| 1,478,253 | 12/1923 | Quenzer | 128/166 |
| 3,613,681 | 10/1971 | Adams | 128/293 |
| 3,892,239 | 7/1975 | Remiro | 128/165 X |

Primary Examiner—Lawrence W. Trapp
Attorney, Agent, or Firm—Huebner & Worrel

[57] ABSTRACT

A tubular support for enclosing a body member therein, the body member being an elastic, generally tubular member having an opening on at least one end. The elastic member is stretchable in all directions so as to provide equal gripping support and pressure to all of the surface of the body member which it encloses. There are facings bonded on the interior and exterior surfaces of the elastic member, the facings having relatively low coefficients of friction and the same stretch rate as the elastic member.

15 Claims, 13 Drawing Figures

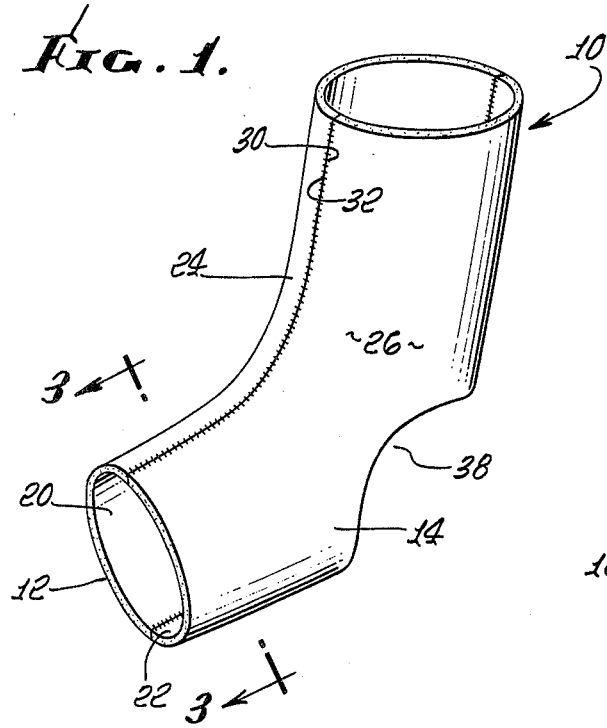
FIG. 1.
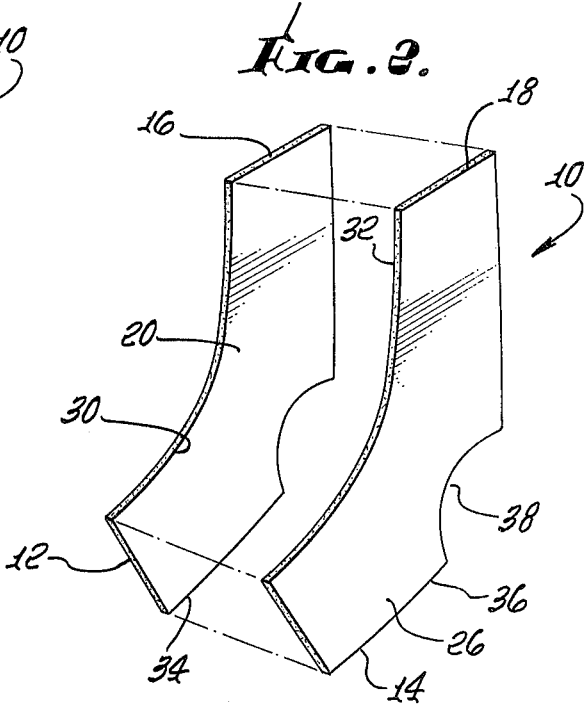
FIG. 2.
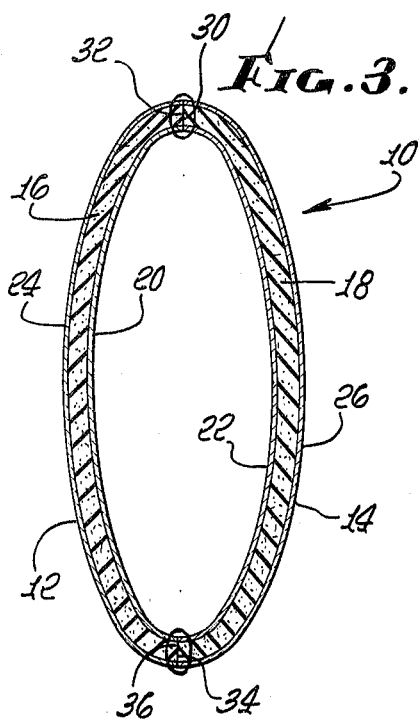
FIG. 3.
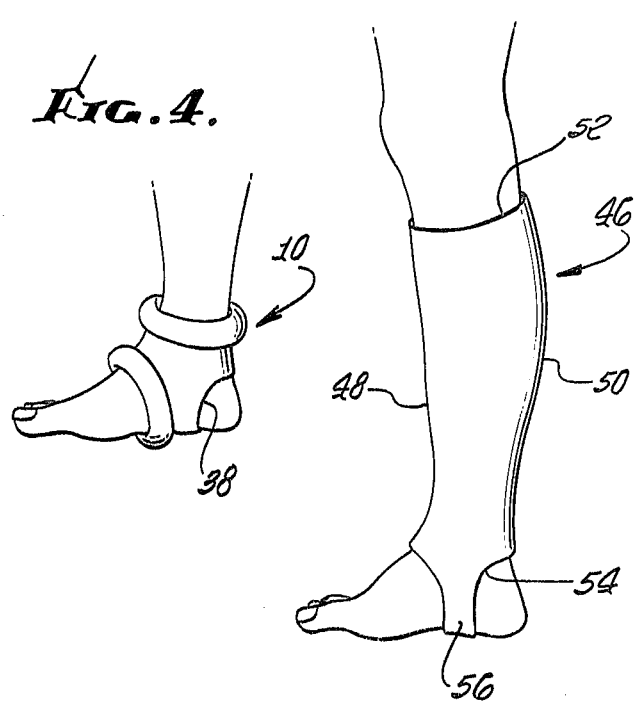
FIG. 4.
FIG. 5.

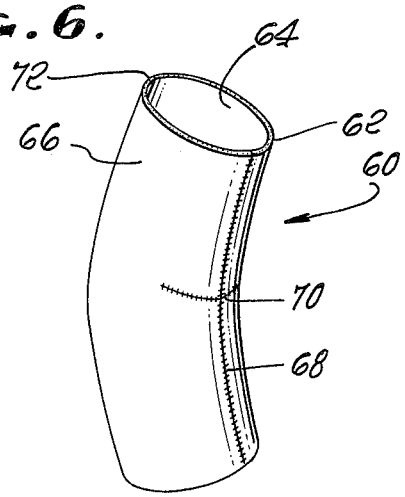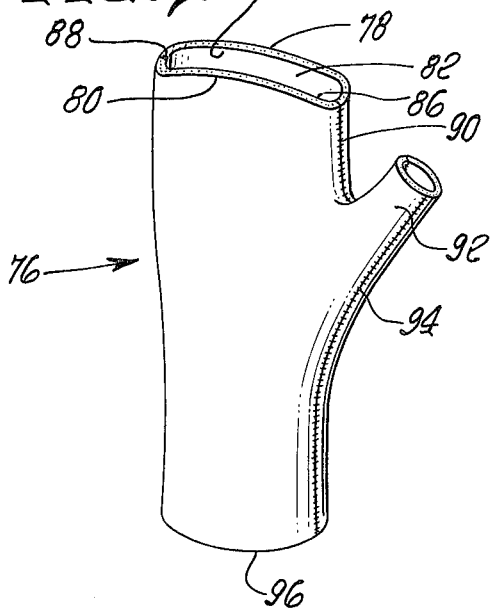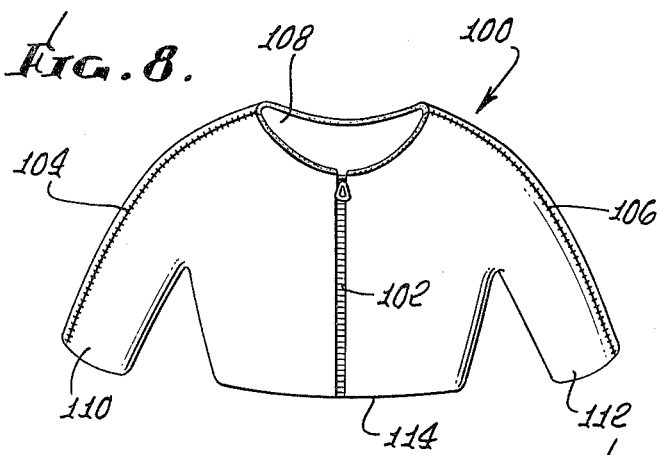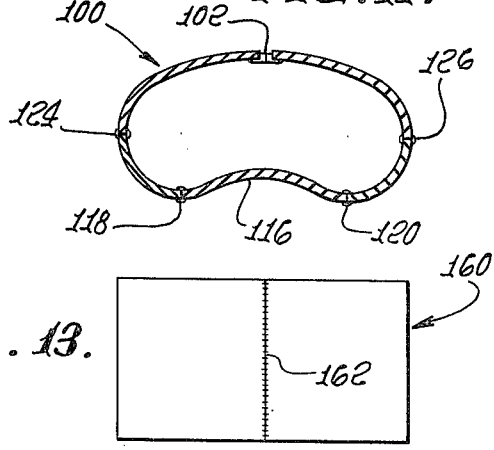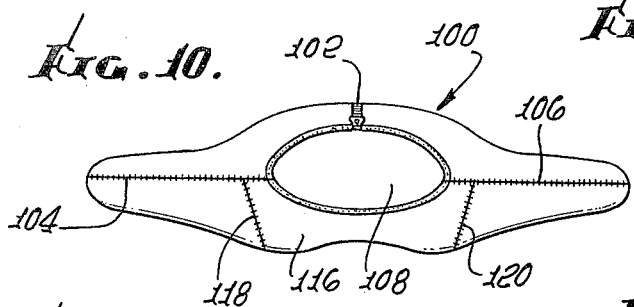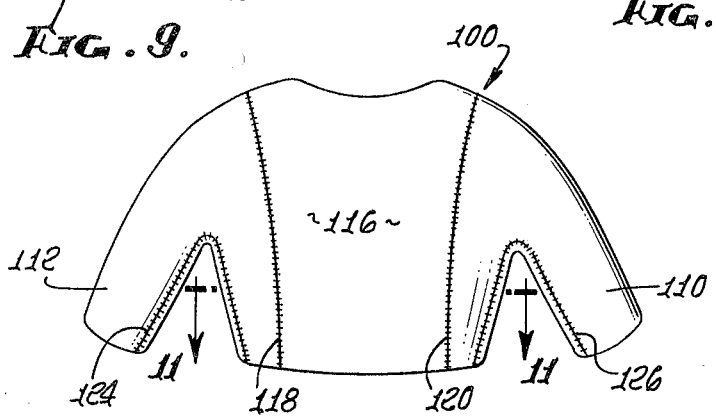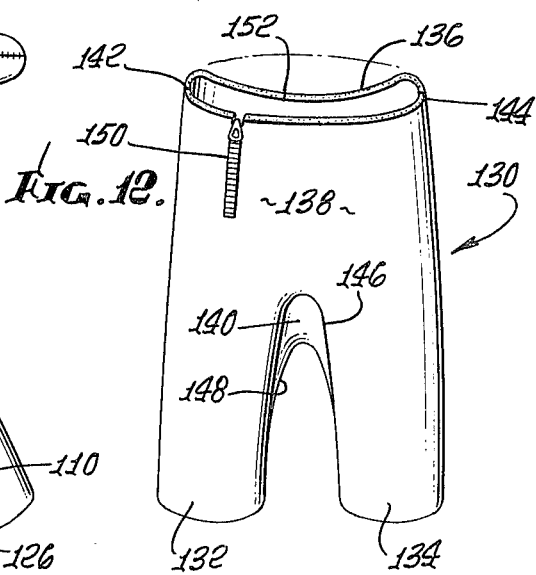

TUBULAR SUPPORT FOR ENCLOSING A BODY MEMBER

BACKGROUND OF THE INVENTION

The present invention relates to support members for the human body or animals for use after fractures, sprains and various back problems, for example.

In the prior art wrapped bandages were typically used for the foregoing problems, but they have the disadvantage of loosening in a very short period of time so as to lose the supporting ability which they were intended to continuously provide. Another type of prior art support is provided in the form of an elastic tube, substantially cylindrical in configuration with no provision, for example, for bending of a knee. In such structures the material gathers under the knee when it is bent so as to loosen, or if it is tight enough to provide adequate support, the gathering tends to cause irritation. This type of support also has the disadvantages of not providing equal, adequate, and continuous pressure on all portions covered thereby.

SUMMARY OF THE INVENTION

The present invention is generally in the form of tubular body support members to be used in the healing of injuries and to be used to protect from new injuries or additional injuries. It is typically made from a closed cell neoprene type rubber which is sold commercially under the trade name "Rubatex" G-23 IN. To this elastomeric material, knit nylon is bonded, so as to form both inner and outer faces. The nylon is made to stretch at the same rate as the elastomeric material.

Support members made as described above have absolute memory and stretch in all directions, providing equal pressure on all portions of the body covered. With such structure the body conforms to the tubular support member.

The foregoing body supports may be made in various thicknesses, such as ⅛ inch and 3/16 inch and in multiple sizes. Where it is used to prevent external traumas, substantially thicker material is used.

Accordingly, it is an object of the present invention to provide an improved tubular elastomeric support member to protect the area supported, and to aid in healing fractures, sprains, and typical upper and lower back problems.

It is another object of the invention to provide tubular body support members, as described in the previous paragraph, which have a very low friction with the epidermis so that the member is easy to put on the body and to remove.

It is still another object of the invention to provide tubular body support members, as described in the previous paragraphs, that have absolute memory, stretch in all directions, and provide continuous equal pressure on all parts of the body covered and intended to be supported.

It is a further object of the invention to provide tubular body support members, as described in the previous paragraphs, which support the body and keep it warm so as to prevent the type of injuries caused by undue expansion of relatively cool tendons and muscles, for example.

It is a still further object of the invention to provide tubular body support members, as described in the previous paragraphs, which may be fitted for use on elbows, knees, the thorax, including the shoulders and upper back, the lumbar and sacral areas, the ankles, and shins in the form of guards, for example. It is also adaptable for use as elbow pads to prevent bed sores on confined patients.

Further objects and advantages of the invention may be brought out in the following part of the specification wherein small details have been described for the competence of disclosure, without intending to limit the scope of the invention which is set forth in the appended claims.

BRIEF DESCRIPTION OF THE DRAWINGS

Referring to the accompanying drawings, which are for illustrative purposes:

FIG. 1 is a perspective view of an ankle support according to the present invention;

FIG. 2 is an exploded view of the embodiment shown in FIG. 1;

FIG. 3 is a cross-sectional view taken along the lines 3—3 in FIG. 1;

FIG. 4 is a view illustrating rolling the support member to put it on or remove it;

FIG. 5 is a view of an embodiment of the invention as a shin guard;

FIG. 6 is a perspective view illustrating a tubular ankle or knee support according to the invention;

FIG. 7 is a perspective view of a hand, thumb and wrist support;

FIG. 8 is a front elevational view of an embodiment of the invention for use on the thorax, shoulders and upper back;

FIG. 9 is a rear elevational view of the embodiment shown in FIG. 8;

FIG. 10 is a plan view of the embodiment shown in FIG. 8

FIG. 11 is a cross-sectional view taken along the lines 11—11 in FIG. 9;

FIG. 12 is a perspective view of a lumbar and sacral support; and

FIG. 13 is an elevational view of a lumbar area support.

DESCRIPTION OF THE PREFERRED EMBODIMENTS

Referring again to the drawings, there is shown in FIGS. 1-4 a tubular support, generally designated as 10, for an ankle. The support 10 is made from two parts, 12 and 14. Each part is comprised of an elastomeric central body 16 and 18, formed of closed cell neoprene rubber, for example. On the interior of the bodies 16 and 18 there are relatively thin knit nylon faces 20 and 22, respectively, and similarly, on the exterior, there are knit nylon facings 24 and 26, respectively. The knit nylon is bonded to elastomeric material which has an absolute memory and stretches in all directions. The nylon stretches at the same rate as the elastomeric material.

The two parts 12 and 14 are secured together to form the tubular support member 10 by bonding and sewing their edges, as 30, 32 and 34, 36 together.

As shown in FIGS. 1 and 3, the resulting configuration is tubular, generally elliptical in cross section, and generally L-shaped in elevation with the outer joint portion of the L-legs removed to form a heel opening 38. The support is shown in position on an ankle in FIG. 4, and has its upper and lower edges rolled, the rolling being only for the purposes of putting on or removing. The nylon provides a very low friction contact with the skin, having a substantially lower coefficient of friction than rubber or cotton, for example.

The efficacy of the support on the ankle and foot, for example, results from the snug stretch fit on the body portion and the equal pressure thereby provided to all portions thereof. Adequate but not excessive tightness is made possible by the low friction of the nylon, the absolute memory of the rubber, and the stretchability in all directions, whereby the body portion conforms to the tube rather than vice versa. The tubular members also keeps the ankle warm to prevent the kind of injury that occurs with cold muscles, and aids in healing any injury. Although the tubular support provides considerable warmth, because the nylon and the rubber breathes, the heat is not excessive and any perspiration is absorbed within the tubular member which is washable. The particular configuration shown extends over the foot and the ankle, and somewhat thereabove, providing an ideal, continuous support in all directions on the area covered to aid in healing ankle injuries and bursitis.

In FIG. 5 a shin guard 46 is shown formed of the same materials as described above, the sewn and bonded edges being at 48 and 50, but they also may be positioned to be at the sides of the leg. The shin guard has an upper opening 52 and a lower opening 54, at which extends an under foot strap 56, the strap being continuous from one side of the lower opening area to the other. The shin guard is made to be relatively thick compared with an ordinary support, which may be typically ⅛ inch or 3/16 inch, the shin guard being ¼ inch or more. This type of guard is particularly adaptable for soccer players, providing excellent leg support, as well as protection against trauma from the exterior thereof.

In FIG. 6 an elbow or knee support 60 is illustrated, the difference as to whether it be for elbow or knee being only in the size. The support 60 is comprised of one piece of the elastic material 62 and the inner and outer nylon facings 64 and 66. There is a main elongated seam 68 extending generally in the direction of the tube and bonded and sewn together. A second seam 70 extends transversely on both sides of the main seam for a fraction of the elliptical surface of the tube. The seam 70 is necessary because material has been cut away whereby the tube is formed to have a concave curve along the main seam, and at the opposite end 72 of the elliptical primary axis, has a convex surface.

The tube 60 is formed generally to fit on the elbow when the arm is in its naturally hanging position, generally curved. Because the material has been cut away at the seam 70, when the elbow or knee is bent there is no gathering of the material on the inside of the bend. Gathering of material is also avoided by the nature of the plastic material which stretches in all directions and exerts the same pressure at all points. The tube 60 is particularly beneficial for treatment and healing of tennis elbow, bursitis in the knee and elbow and torn meniscus in the knee.

In FIG. 7 a hand, wrist and thumb support 76 is shown. The upper end of the support has convexly extending edges 78 and 80 which follow the contour of the knuckle bones of the hand, the upper end opening 82 having a slot configuration with inwardly concaved inner edges 84 and 86 formed at the opposing seams 88 and 90, the seams being sewn and bonded.

A tubular elliptical thumb portion 92 extends outwardly from the member 76 and upwardly toward the opening 82. The thumb member is closed at the seam 90 and the seam 94. The lower portion 96 and the lower opening are elliptical.

The tubular member 76 acts as a wrist support as well as a hand and thumb support and supports the thumb against movement, which movement would cause pain in an injuried wrist.

In FIGS. 8–11, a generally tubular member 100 is shown to be adapted to fit over the thorax, shoulders, the upper back, and the upper arms. The support member 100 has a zippered opening 102 extending vertically along the entire front. Bonded and sewn seams 104 and 106 extend from the low fitting neck opening 108. Immediately outwardly of the neck opening, the support member fits on the shoulders and extends down to cover and support the arms, the sleeves 110 and 112 being long enough to extend to the lower end 114 of the support, which is adapted to fit transversely across the sternum area.

An insert panel 116 is sewn and bonded into the back at the seams 118 and 120. This insert is provided to be fitted where material has been cut away to make the back narrower than the chest portion so that the support holds the shoulders rearwardly and generally erect, the body conforming to the support. The lower end opening has the general configuration of the cross-sectional view shown in FIG. 11. Inner seams 124 and 126 extend along the inner sleeve portions and along the body portion, extending downwardly to the horizontal level of the sternum.

The generally tubular thorax support 100 is adapted to support the chest, the shoulders and the upper back, and the sleeves extend downwardly to the level of the sternum to support the arms as necessary with some shoulder and back conditions. The support 100 is beneficial for bursitis in the shoulder and fractures of the shoulder and collar bones. The support keeps the entire area warm so as to prevent movement of cool muscles and tendons, for example.

In FIG. 12 high-waisted, generally tubular pants 130 are shown. This support extends upwardly in the front and back to the sternum area, and the legs 132, 134 are adapted to extend just above the knees. The support is formed with three pieces, a back 136, a front 138 and a gusset 140. They are joined together by bonded and sewn seams at 142, 144, 146 and 148. The front has a zipper 150 at the side so as to not interfere with covering clothing at the front where the zipper would tend to protrude. The top of the back 152 is cut lower than the front so as to better conform to the body.

This supports the lumbar and sacral areas and, therefore, extends upwardly to the sternum and downwardly to just above the knees to give all the areas covered support, and to keep them warm to avoid damaging movements of cool muscles.

The support 130, as the other supports shown, comes in various sizes and thicknesses of the same materials and is adapted to fit closely and comfortably while adequately supporting the lower back below the sternum level.

In FIG. 13, there is shown a one piece tubular lumbar support 160, generally rectangular in elevation and in plan view it has a configuration similar to that in FIG. 11. The support is bonded and sewn at 162.

The tube 160 is adapted to extend downwardly from the sternum over the lower back. In addition to general back healing, it provides excellent support for drivers of automobiles and trucks over long periods of driving.

The invention and its attendant advantages will be understood from the foregoing description and it will be apparent that various changes may be made in the form, construction and arrangements of the parts of the invention without departing from the spirit and scope thereof or sacrificing its material advantages, the arrangements hereinbefore described being merely by way of example. I do not wish to be restricted to the specific forms shown or uses mentioned except as defined in the accompanying claims, wherein various portions have been separated for clarity of reading and not for emphasis.

I claim:

1. A tubular support for enclosing a body member, comprising:
   an elastic generally tubular member having an opening for receiving a body member,
   said elastic member being stretchable in all directions, and
   a facing on the interior surface of said elastic member having a relatively low coefficient of friction,
   said facing having the same stretch rate in all directions as the elastic member and being free of tension when not stretched on the body member,
   said facing and elastic member having absolute memory and constant equal gripping pressure on all parts of the body member covered and intended to be supported.

2. The invention according to claim 1 in which:
   said facing is a sheet of knitted nylon bonded to the elastic member.

3. The invention according to claim 2 in which:
   a sheet of said knitted nylon is bonded to the exterior of said elastic member to form an outer facing.

4. The invention according to claim 3 in which:
   said inner facing has a coefficient of friction with epidermis lower than rubber and cotton.

5. The invention according to claim 4 in which:
   said elastic member is formed of two parts sewn and bonded together along elongated opposing edges,
   said opening being at one end and a second opening being at the other end,
   said openings and said elastic member being generally elliptical.

6. The invention according to claim 5 in which:
   said elastic member and facings are generally L-shaped, and
   the outer joint of the L-legs being removed to form a heel opening whereby said elastic member is adapted to fit over ankle and foot portions.

7. The invention according to claim 2 in which:
   said elastic member is cellular rubber having closed cells,
   said elastic member being substantially thicker than said facing.

8. The invention according to claim 1 in which:
   said facing has a coefficient of friction with epidermis lower than rubber.

9. The invention according to claim 1 in which:
   said facing has a coefficient of friction with epidermis lower than cotton.

10. The invention according to claim 4 in which:
    said elastic member is formed of two parts sewn and bonded together along elongated opposing edges,
    said opening being at one end and being generally slot-shaped having inwardly concave ends,
    a second opening at the other end of the elastic member and being generally elliptical, and
    a tubular thumb engaging member extending outwardly from one of said opposing edges,
    said thumb member extending upwardly in the direction of said opening at said one end but away therefrom,
    said opening at said one end having generally convex edges bowing outwardly from said concave ends.

11. The invention according to claim 4 in which:
    said elastic member has a sewn and bonded seam in the elongated direction on one side thereof,
    said opening being at one end and a second opening being at the other end,
    said openings and said elastic member being generally elliptical,
    said elastic member being curved along the elongated direction so as to be concave on said one side and convex on an opposing side,
    a bonded and sewn seam transverse to said seam in the elongated direction, extending on both sides of the elongated seam for a fraction of the circumference of the tubular member.

12. The invention according to claim 4 in which:
    said opening being at one end and a second opening being at the other end, and
    a strap extending outwardly away from said other end in the elongated direction of said elastic tubular member,
    said strap being continuous from one side of said tubular member to an opposite side thereof outwardly of said second opening.

13. The invention according to claim 4 in which:
    said elastic member is formed of at least two parts sewn and bonded together along elongated edges,
    said opening being at one end and being adapted to fit around a lower part of the neck of the wearer,
    a second lower opening adapted to extend around the sternum area, the elastic member being adapted to extend upwardly from the sternum level and over the shoulders and back,
    sleeves for the arms extending downwardly from the shoulders to approximately the sternum level,
    a sewn and bonded back panel adapted to narrow the back on comparison with the chest to hold the shoulders rearwardly and the back generally erect, and
    a zippered front opening extending from the neck opening to the sternum.

14. The invention according to claim 4 in which:
    said elastic member is formed of at least two parts sewn and bonded together along elongated edges to form high waisted pants,
    said opening being at the upper end of the pants and being adapted to fit approximately at the level of the sternum,
    the back of the pants being cut to fit lower than the front and the lower end of the legs having openings just above the knees,
    a gusset sewn and bonded in the crotch, and
    a zippered opening near a side of the front.

15. The invention according to claim 1 in which:
    said elastic member is formed from a sheet sewn and bonded together along opposing edges.

* * * * *